United States Patent
Op Den Buijs et al.

(10) Patent No.: US 9,451,905 B2
(45) Date of Patent: Sep. 27, 2016

(54) METHOD AND APPARATUS FOR MONITORING THE BARORECEPTOR REFLEX OF A USER

(71) Applicant: KONINKLIJKE PHILIPS N.V., Eindhoven (NL)

(72) Inventors: Jorn Op Den Buijs, Eindhoven (NL); Maartje Helena Schonenberg, Eindhoven (NL); Steffen Clarence Pauws, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 105 days.

(21) Appl. No.: 14/367,243

(22) PCT Filed: Dec. 7, 2012

(86) PCT No.: PCT/IB2012/057049
§ 371 (c)(1),
(2) Date: Jun. 20, 2014

(87) PCT Pub. No.: WO2013/093690
PCT Pub. Date: Jun. 27, 2013

(65) Prior Publication Data
US 2014/0358017 A1 Dec. 4, 2014

Related U.S. Application Data

(60) Provisional application No. 61/577,740, filed on Dec. 20, 2011.

(51) Int. Cl.
*A61B 5/11* (2006.01)
*A61B 5/00* (2006.01)
(Continued)

(52) U.S. Cl.
CPC .......... *A61B 5/1116* (2013.01); *A61B 5/02444* (2013.01); *A61B 5/1102* (2013.01);
(Continued)

(58) Field of Classification Search
CPC . A61B 5/1116; A61B 5/6891; A61B 5/1128; A61B 5/11102; A61B 5/1115
See application file for complete search history.

(56) References Cited

U.S. PATENT DOCUMENTS 7,141,026 B2    11/2006  Aminian et al.
2007/0161912 A1  7/2007  Zhang et al.
(Continued)

FOREIGN PATENT DOCUMENTS

WO    2008104918 A1      9/2008
WO    WO 2008/104918  *  9/2008
WO    2010029466 A1      3/2010

OTHER PUBLICATIONS

Cennini, G. et al. "Heart rate monitoring via remote photoplenthysmography with motion artifacts reduction", pp. 4867-4875, Mar. 1, 2010, vol. 18, No. 5, Optics Express.
(Continued)

*Primary Examiner* — George Evanisko

(57) ABSTRACT

There is provided an apparatus for use in monitoring the baroreceptor reflex in a user, the apparatus comprising a processor configured to process a signal output by a first sensor that is attached to or located proximate to a bed to determine when the user moves from a lying position on the bed to a sitting position, and to provide an indication of the baroreceptor reflex of the user by processing the signal to determine the change in the heart rate of the user that occurs as a result of moving from the lying position to the sitting position.

15 Claims, 3 Drawing Sheets

(51) Int. Cl.
*A61B 5/024* (2006.01)
*G08B 21/04* (2006.01)

(52) U.S. Cl.
CPC ............ *A61B5/1115* (2013.01); *A61B 5/1128* (2013.01); *A61B 5/6891* (2013.01); *A61B 5/7267* (2013.01); *G08B 21/0492* (2013.01)

(56) References Cited

U.S. PATENT DOCUMENTS

2007/0213619 A1 9/2007 Linder
2010/0217139 A1 8/2010 Pinter et al.
2011/0112442 A1 5/2011 Meger et al.

OTHER PUBLICATIONS

Poh, M-Z et al. "Non-contact, automated cardiac pulse measurements using video imaging and blind source separation". Optics Express, vol. 18, No. 10, 2010.
Heisele, B. et al. "Face Recognitiion with support vector machines: global versus component based approach", Computer Vision, 2001.
Allin, S. et al. "Sit to stand detection and analysis", AAAI Fall Symposium Series 2008.
Jones et al, "Changes in Heart Rate and R-Wave Amplitude With Posture", Chinese Journal of Physiology, vol. 46, No. 2, 2003, pp. 63-69.
He et al, A Continuous, Wearable, and Wireless Heart Monitor Using Head Ballistocardiogram (BSG) and Head Electrocardiogram (ECG), 33rd Annual Interanntional Conference of the IEEE EMBS, 2011, p. 4729-4732.

* cited by examiner

METHOD AND APPARATUS FOR MONITORING THE BARORECEPTOR REFLEX OF A USER

This application is a national stage application under 35 U.S.C. §371 of International Application No. PCT/IB2012/057049 filed on Dec. 7, 2012 and published in the English language on Jun. 27, 2013 as International Publication No. WO/2013/093690, which claims priority to U.S. Application No. 61/577,740 filed on Dec. 20, 2011, the entire disclosures of which are incorporated herein by reference.

BACKGROUND TO THE INVENTION

The invention relates to a method and apparatus for providing an indication of the baroreceptor reflex of a user, and in particular provides a method and apparatus that can provide an indication of the baroreceptor reflex of the user using non-invasive and contactless measurements.

BACKGROUND TO THE INVENTION

When a person moves from a supine posture to a sitting or standing posture, pooling of blood in the abdomen and legs occurs due to gravity, which causes a diminished venous return to the heart, and therefore a diminished cardiac output and cerebral perfusion. Normally, the baroreceptors (pressure sensors in the wall of the carotid artery and aorta) sense the decrease in blood pressure and subsequently stimulate the sympathetic nervous system, causing a transient increase in heart rate of approximately 10 to 30 beats per minute. Due to the transient increase in heart rate, cardiac output and cerebral perfusion remains at a normal level. However, when the sensitivity of this baroreceptor reflex (also referred to as baroreflex) is reduced, there is an abnormal change in blood pressure and a diminished or absence of a transient increase in heart rate upon moving from a supine posture to a standing posture. In this case, blood pressure and cerebral perfusion substantially decrease upon moving from a supine posture to a sitting or standing posture, which can lead to a person feeling lightheaded, fainting or falling after standing up quickly.

The baroreceptor reflex and the ability to maintain blood pressure immediately after standing up deteriorate with age, causing symptoms including lightheadedness, confusion, nausea, and fainting. However, this orthostatic intolerance can also be asymptomatic. It is desirable to be able to routinely monitor heart rate changes when moving from a supine or lying posture to a sitting and/or standing posture, as this would enable the analysis of trends in the baroreceptor reflex under the natural conditions for standing up. It is thought that trend monitoring of the baroreceptor reflex and orthostatic intolerance could aid medical professionals in diagnosing underlying (chronic) disease, such as diabetes or heart failure. Timely detection of the deterioration of the baroreceptor reflex by a medical professional could facilitate intervention and potentially prevent falls and faints. Furthermore, monitoring trends in the baroreceptor reflex could be used to assess the effects of nutrition and medications that are known to improve or worsen orthostatic intolerance, such as salt and fluid intake, beta-blockers and anti-hypertensive drugs.

A reduced baroreceptor reflex may be assessed by a medical professional using various orthostatic stress tests during which blood pressure, heart rate and respiration rate are continuously monitored. Such tests include standing up, head-upright tilt (HUT) table testing, and the use of lower body negative pressure. However, such tests require visits to a medical facility, are generally not performed on a routine basis, are not standardized, and the results are often not repeatable. Furthermore, orthostatic stress tests, such as HUT are unnatural because the tilting of the patient does not resemble the real world scenario of the person standing up. In addition, the test considers a person that has been resting on a tilt table for some time (e.g., 15 minutes) at some point during the day, whereas it is preferable to evaluate orthostatic intolerance on a routine basis at a regular time in the morning, e.g. when getting up out of bed. Finally, orthostatic stress tests are clearly obtrusive and (mental) stress during the procedures influences the test results.

It is possible for a person to self-test using a blood pressure cuff and a heart rate monitor to measure the blood pressure and heart rate upon standing up from a sitting or supine position, but this is inconvenient and time consuming for the person. Furthermore, it is known that blood pressure measurements taken from a person in a lying position rely heavily on the exact position of the cuff, as well as the arm position. Such precise measurements cannot be expected from measurements taken in the home environment.

US 2007/0161912 describes the analysis of a baroreceptor reflex on standing up from a sitting or supine position using a device that includes a heart rate sensor and a posture sensor. However, this device needs to be implanted in the patient's body and requires a sensor to be placed in or around an artery or vein and/or electrodes to be attached to the patient's heart. Therefore, this device is not particularly suited to general usage by medical practitioners, and requires the patient to undergo a significant surgical procedure in order for the device to be implanted.

Other devices are known that can be used to detect the increase (or the absence of an increase) in heart rate upon standing and include devices that are placed in contact with the body, including a pulse oximeter or a heart rate watch, but these require the patient to remember to wear such devices, and may be uncomfortable to the patient while they are sleeping.

Therefore, there is a need for an apparatus and method for monitoring the baroreceptor reflex that can provide an indication of the baroreceptor reflex of the user using non-invasive and contactless measurements.

SUMMARY OF THE INVENTION

According to a first aspect of the invention, there is provided an apparatus for use in monitoring the baroreceptor reflex in a user, the apparatus comprising a processor configured to process a signal output by a first sensor that is attached to or located proximate to a bed to determine when the user moves from a lying position on the bed to a sitting position, and to provide an indication of the baroreceptor reflex of the user by processing the signal to determine the change in the heart rate of the user that occurs as a result of moving from the lying position to the sitting position.

In a preferred embodiment, the processor is configured to determine the change in the heart rate of the user that occurs as a result of moving from the lying position to the sitting position as the change in the heart rate determined while the user is in a lying position on the bed to the maximum heart rate that occurs as a result of moving from the lying position to the sitting position.

Preferably, the first sensor is configured to be attached to a bed and output a signal representing the movements of a user on the bed to the processor. In this way, the user can be monitored unobtrusively.

The first sensor can be a strain sensor, a strain gauge, a pressure sensor, a piezoelectric sensor, a resistive force sensor, a load cell, an electret foil sensor, a sensor for optically sensing movement-induced changes in a part of the bed, a camera or a Doppler radar sensor.

Preferably, the processor is configured to process signals output by an array of first sensors that are attached to or located proximate to the bed to determine when the user moves from a lying position on the bed to a sitting position. The use of an array of sensors allows the position of the user on the bed, and their posture, to be easily determined.

In preferred embodiments, the processor is further configured to process a signal output by a second sensor that is located proximate to the bed to determine when the user moves to a standing position, and to provide an indication of the baroreceptor reflex of the user by processing the signal from the second sensor to determine the change in the heart rate of the user that occurs as a result of moving from the sitting position to the standing position.

Preferably, the processor is configured to determine the change in the heart rate of the user that occurs as a result of moving from the sitting position to the standing position as the change in the heart rate determined while the user is in the sitting position to the maximum heart rate that occurs as a result of moving from the sitting position to the standing position.

Preferably, the processor is further configured to determine the change in the heart rate determined while the user is in the lying position on the bed to the maximum heart rate that occurs as a result of moving from the lying position to the standing position.

In a preferred embodiment, to reduce the power consumption of the apparatus, the processor is configured to activate the second sensor when it is determined that the user has moved from a lying position on the bed to a sitting position.

In some embodiments, the second sensor is configured to be located near to the bed and to measure the movements of the user while they are in a standing position.

The second sensor can be a camera or a Doppler radar sensor (where the first sensor is not also a camera or Doppler radar sensor), a sensor for optically sensing movement-induced changes in a mat near to the bed or a mechanical sensor such as a strain sensor, a strain gauge, a pressure sensor, a piezoelectric sensor, a resistive force sensor, a load cell or an electret foil sensor.

In some embodiments, the processor is configured to calibrate the signal output by the second sensor when the user is in a sitting position on the bed using the heart rate determined from the signal output by the first sensor when the user is in the sitting position.

In further embodiments, the processor is further configured to process the signal output by the first sensor to determine the respiration rate of the user. The respiration rate can be used as a further indication of the baroreceptor reflex of the user.

According to a second aspect of the invention, there is provided a method of monitoring the baroreceptor reflex in a user, the method comprising receiving measurements from a first sensor attached to or located proximate to a bed; processing the measurements to determine when the user moves from a lying position on the bed to a sitting position; and providing an indication of the baroreceptor reflex of the user by processing the measurements to determine the change in the heart rate of the user that occurs as a result of moving from the lying position to the sitting position.

Preferably, the step of providing an indication of the baroreceptor reflex of the user comprises determining the change from the heart rate determined while the user is in a lying position on the bed to the maximum heart rate that occurs as a result of moving from the lying position to the sitting position.

Preferably, the step of receiving measurements comprises receiving measurements from a first sensor attached to a bed, the first sensor outputting measurements of the movements of a user on the bed.

Preferably, the first sensor is a strain sensor, a strain gauge, a pressure sensor, a piezoelectric sensor, a resistive force sensor, a load cell, an electret foil sensor, a camera or a Doppler radar sensor.

Preferably, the step of receiving measurements comprises receiving measurements from an array of first sensors that are attached to or located proximate to the bed, and the step of processing the measurements to determine when the user moves from a lying position on the bed to a sitting position comprises processing the measurements received from the array of first sensors.

Preferably, the method further comprises the steps of receiving measurements from a second sensor that is located proximate to the bed; and processing the measurements to determine when the user moves to a standing position, and wherein the step of providing an indication of the baroreceptor reflex of the user further comprises processing the measurements from the second sensor to determine the change in the heart rate of the user that occurs as a result of moving from the sitting position to the standing position.

Preferably, the step of providing an indication of the baroreceptor reflex of the user comprises determining the change in the heart rate of the user that occurs as a result of moving from the sitting position to the standing position as the change from the heart rate determined while the user is in the sitting position to the maximum heart rate that occurs as a result of moving from the sitting position to the standing position.

Preferably, the step of providing an indication of the baroreceptor reflex of the user further comprises determining the change from the heart rate determined while the user is in the lying position on the bed to the maximum heart rate that occurs as a result of moving from the lying position to the standing position.

Preferably, the method further comprises the step of activating the second sensor when it is determined that the user has moved from a lying position on the bed to a sitting position.

Preferably, the second sensor is a camera or a Doppler radar sensor (where the first sensor is not also a camera or Doppler radar sensor) or a mechanical sensor such as a strain sensor, a strain gauge, a pressure sensor, a piezoelectric sensor, a resistive force sensor, a load cell or an electret foil sensor.

Preferably, the method further comprises the step of calibrating the measurements output by the second sensor when the user is in a sitting position on the bed using the heart rate determined from the measurements received from the first sensor when the user is in the sitting position.

Preferably, the step of providing an indication of the baroreceptor reflex of the user further comprises processing the measurements received from the first sensor to determine the respiration rate of the user.

According to a third aspect of the invention, there is provided a computer program product, comprising computer readable code embodied therein, the computer readable code being configured such that, upon execution by a suitable processor or computer, the processor or computer performs the method as described in any of the preceding paragraphs.

BRIEF DESCRIPTION OF THE DRAWINGS

Embodiments of the invention will now be described, by way of example only, with reference to, and as shown in, the following drawings, in which.

DETAILED DESCRIPTION OF THE PREFERRED EMBODIMENTS

Figure 1:
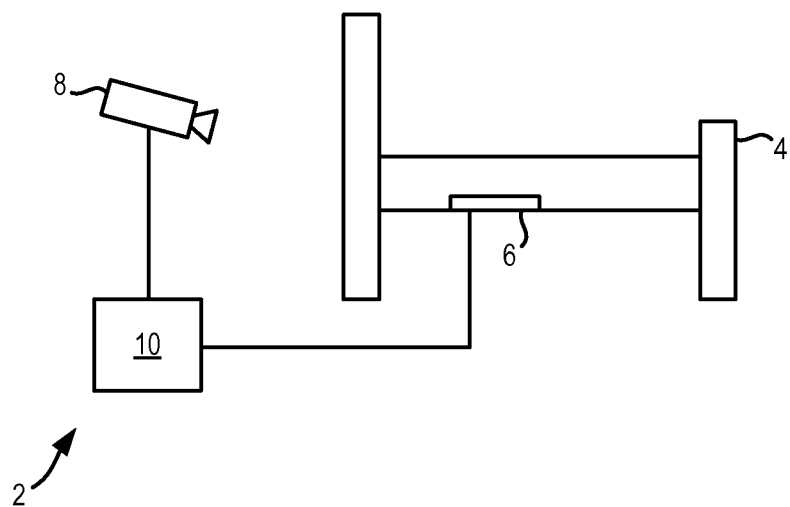
FIG. 1 shows a bed and an apparatus according to a first embodiment of the invention.

An apparatus according to a first embodiment of the invention is shown in FIG. 1. The apparatus 2 is for use with a bed 4, such as a hospital bed or a bed in the home of the user of the apparatus 2. According to this embodiment, the apparatus 2 comprises two sensors 6, 8, the first sensor being a sensor 6 that is attached to the bed 4 and that measures the movements of the user while the user is lying or sitting on the bed, and the second sensor is a camera 8 that is located near to the bed 4 and that records images of the user while they are sitting on and standing next to the bed 4.

In this embodiment, the first sensor 6 can be a mechanical sensor 6 that preferably comprises one or more strain sensors or strain gauges that are integrated into the slats of the bed 4. Alternatively, the one or more strain sensors or strain gauges can be located on a different part of the bed 4, such as in the mattress, in or under the bed posts, or elsewhere in the bed frame. In alternative embodiments, other types of mechanical sensors can be used for measuring heart rate and body posture that are sensitive to small vibrations generated by the cardio-pulmonary function and other muscle activities of the user, such as pressure sensors, piezoelectric sensors, resistive force sensors, load cells, and electret foil sensors. In the preferred and alternative embodiments, an array of sensors 6 is preferably used such that different sensors 6 are placed at different locations in the bed 4 to enable more accurate detection of heart rate and body position (lying down vs. sitting upright on the edge of the bed 4).

The apparatus 2 also comprises a control unit 10 that is connected to the mechanical sensor 6 and camera 8. The control unit 10 processes the signal output by the mechanical sensor 6 to determine the posture of the user on the bed 4 (so either lying down or sitting upright) and to detect the heart beats of the user. From this, the control unit 10 can determine the heart rate of the user while they are lying on the bed 4 (for example in a supine position, a prone position or lying on their side), when the user moves from a lying posture to a posture in which they are sitting on the edge of the bed 4, and the heart rate of the user while they are sitting on the edge of the bed 4.

The control unit 10 processes the images collected by the camera 8 to determine the posture of the user (in particular whether the user is sitting on the bed 4 or standing near to the bed 4) and to detect the heart rate of the user. In detecting the heart rate of the user, the camera 8 and the associated processing of the control unit 10 act as a remote photoplethysmograph (PPG), for example as described in "Heart rate monitoring via remote photoplethysmography with motion artifacts reduction" by G. Cennini, J. Arguel, K. Aksit and A. van Leest, pages 4867-4875, 1 Mar. 2010, Vol. 18, No. 5, Optics Express, the content of which is hereby incorporated by reference. Alternatively, the control unit 10 can process images of the user's face obtained using the camera 8 to recover the cardiac pulse rate, as described in "Non-contact, automated cardiac pulse measurements using video imaging and blind source separation". M-Z Poh, D J McDuff and R W Picard Optics Express Vol. 18, No. 10, 2010, the content of which is hereby incorporated by reference.

Briefly, in remote PPG, the detection of heart rate from camera images obtained under ambient light is based on the volumetric changes in the facial blood vessels that result from the cardiac cycle. These volumetric changes alter the path length of incident ambient light. The subsequent changes in amount of reflected light indicate the timing of the cardiac cycle. By recording a video of the facial region with a digital camera 8, the red green blue (RGB) color sensors pick up a mixture of the reflected plethysmographic signal along with other sources of fluctuations in light due to artifacts, such as motion and changes in ambient lighting conditions.

The three RGB signals are recorded in a region of interest (e.g., a rectangular region inside the facial region) and spatially averaged. The spatially averaged RGB signals are processed in time-windows with a length of e.g. 30 seconds, with overlap. The signals are normalized by subtracting the mean and dividing by the standard deviation. Motion reduction algorithms, such as independent component analysis, are then applied to the signals to filter out the motion artifacts. The frequency spectrum of the filtered signal is then computed, e.g., using the fast Fourier transform, and heart rate is determined as the frequency at a (local) maximum in the spectrum.

Previously, PPG has always been implemented using special light sources, but recent advances in this field have shown that accurate pulse measurements can be achieved using a commercially available digital camcorder or camera under conditions of ambient light. Since the PPG signal is very sensitive to motion (particularly in the case of contactless measurements), the underlying processing algorithms need to be capable of filtering out these artifacts. As motion artifacts and heart rate are typically in the same frequency bandwidth, non-linear filters are necessary to reduce motion artifacts.

From this, the control unit 10 can determine the heart rate of the user while they are sitting on the bed 4 (for example for comparison with the heart rate determined using the mechanical sensor 6), when the user moves from the sitting posture to an upright (standing) posture, and the heart rate of the user when they are standing by the bed 4.

The control unit 10 combines the determined heart rates and posture information to provide an indication of the baroreceptor reflex of the user.

Figure 2:
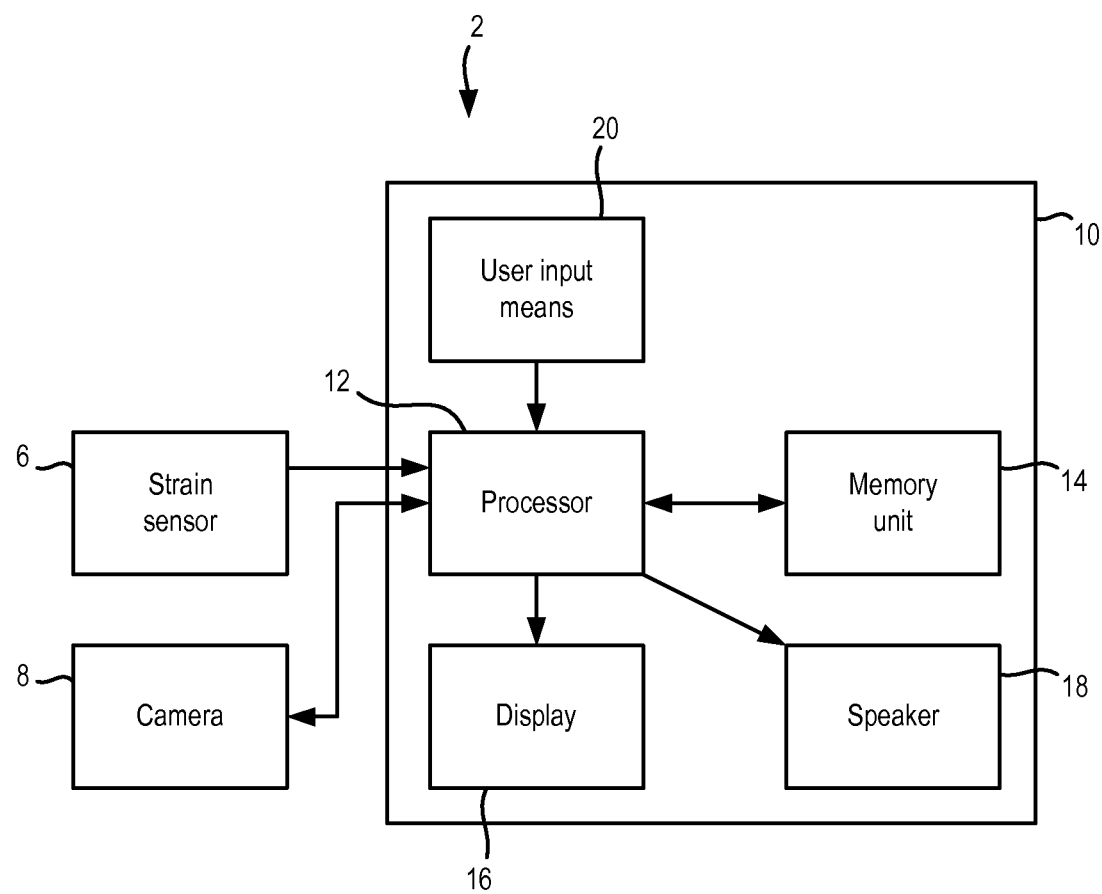
FIG. 2 is a block diagram of an apparatus according to the first embodiment of the invention.

FIG. 2 shows the apparatus 2 of FIG. 1 in more detail. In particular, the control unit 10 comprises a processor 12 that receives the signal output from the mechanical (strain) sensor 6 and camera 8 and that performs the processing of the signals outlined above. The control unit 10 also comprises a memory unit 14 that is connected to the processor 12 and that can store, for example, the signals received from the mechanical sensor 6 and camera 8 and program code for execution by the processor 12 to perform the processing required to determine the indication of the baroreceptor reflex from the signals.

In this illustrated embodiment, the control unit 10 also comprises a display 16 which the processor 12 can control to display the indication of the baroreceptor reflex, current and historical measurements of the heart rate of the user, the current and historic measurements of the posture of the user, an alert that the heart rate of the user is abnormal (e.g. including a lack of (a sufficient) heart rate increase when the user moves from a lying position to a sitting or standing position) and therefore the user might be at risk of falling or fainting, and/or any other information that might be of use to the user or a medical professional. The control unit 10 further comprises a speaker 18 that the processor 12 can control to output an audible tone or message to the user to alert them that they are at risk of falling or fainting in response to determining that the user has had an abnormal baroreceptor reflex during a particular posture change.

The processor 12 can also optionally prepare reports for use by a medical professional from the measurements collected during operation of the apparatus 2 and output these on the display 16, or via a communication interface (such as a wired or wireless connection) to a computer terminal of the medical professional.

Finally, the control unit further comprises user input means 20 which allows the user to control the operation of the apparatus 2 and to input required information to the control unit 10. The user input means 20 can include, but is not limited to, a keyboard, a keypad, a mouse and a touch panel (for example associated with display 16). The user input means 20 may also include a microphone so that the user can record messages relating to their current status for subsequent review by their medical professional. For example, the user can use the microphone to record a message indicating that they have just had a fall, or that they have fainted or had lightheadedness after moving from a lying position to a sitting or standing position.

Although the mechanical sensor 6, camera 8 and control unit 10 are shown as distinct units in FIGS. 1 and 2, it will be appreciated that it is possible for the control unit 10 to be integrated with the mechanical sensor 6 or camera 8.

Figure 3:
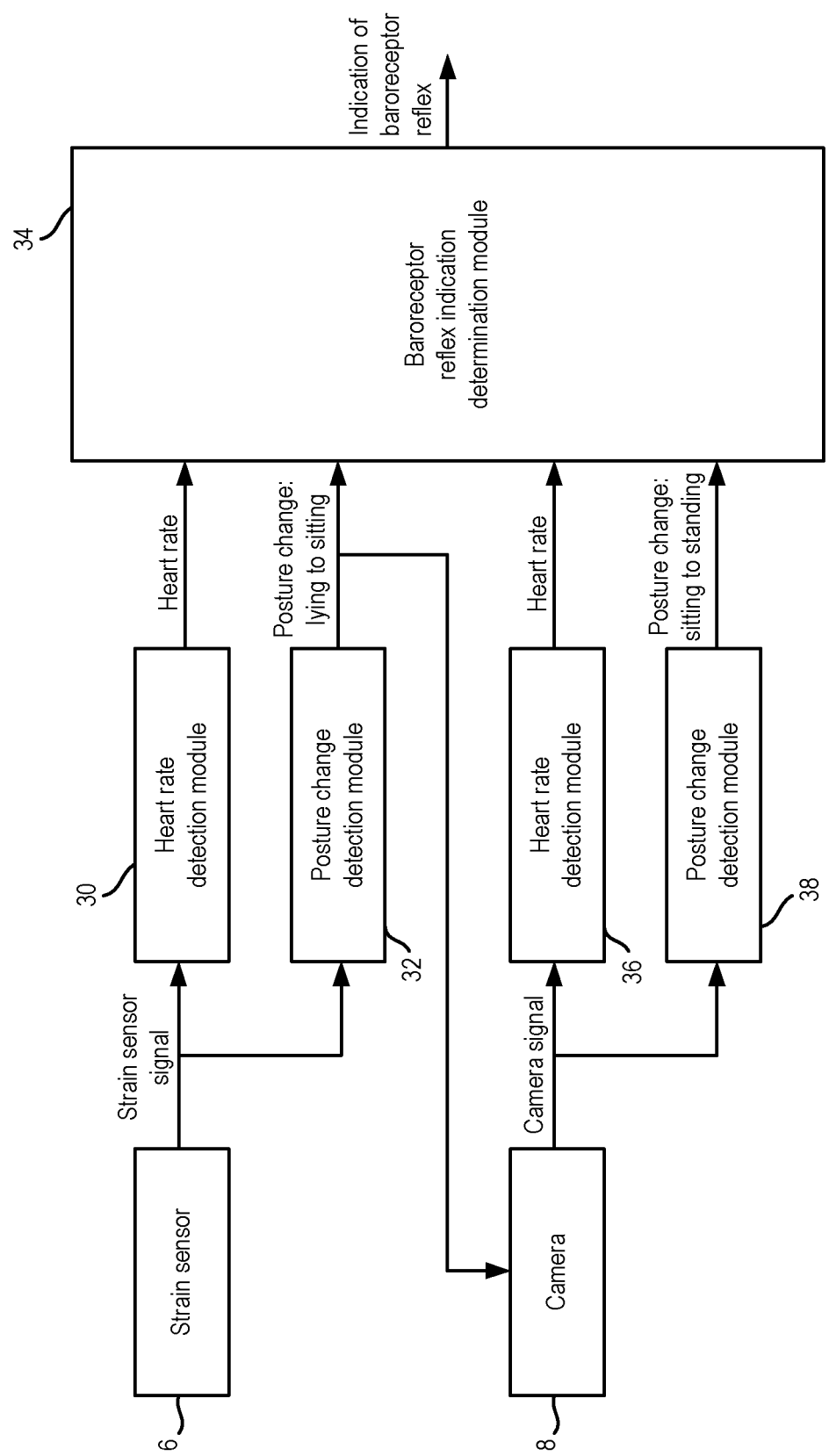
FIG. 3 is a block diagram illustrating the processing steps performed in the first embodiment of the invention.

FIG. 3 illustrates the processing steps performed by the processor 12 in the first embodiment of the invention to determine an indication of the baroreceptor reflex. In FIG. 3, the processing steps are illustrated as being implemented by a number of distinct processing modules, and it will be appreciated that the modules can be implemented as separate hardware processing modules in the processor 12, by suitable program code that is executed by the processor 12, or by any combination thereof.

In FIG. 3, the signal output by the mechanical (strain) sensor 6 is provided to a heart rate detection module 30 and a posture change detection module 32. The heart rate detection module 30 processes the mechanical (strain) sensor signal to extract the heart rate of the user while they are lying or sitting on the bed 4. The detected heart rate of the user is output by the heart rate detection module 30 to a baroreceptor reflex indication determination module 34. Those skilled in the art will be aware of suitable algorithms that can be used in the heart rate detection module 30 to detect the heart rate of the user in the signals received from the mechanical sensor(s) 6. In particular, as the mechanical sensor(s) 6 provide measurements of the ballistic forces in the user's body that result from the pumping of blood by the heart, the signals from the mechanical sensor(s) 6 can be processed using algorithms used in ballistocardiography. In these algorithms, the detection of the heart rate from the signal from the mechanical sensor(s) 6 (whether a strain gauge, piezo-electric sensor, pressure sensor, load cell, etc.) involves amplifying, low-pass filtering and sampling of the analogue sensor signal. The digital signal is then filtered using a low-pass or band-pass filter. For example, a band-pass filter can be designed such that the target heart rate is constrained within 35 to 180 beats per minute. The heart peaks are then detected by exploring the local minima (or maxima) in the signal within a moving window, or by analyzing the autocorrelation function in the frequency domain. The optimal window length for performing a fast Fourier transform can be computed from the preceding beat-to-beat interval, and needs to span several beats, depending on the type and number of sensors 6 (in the case of an array of sensor 6).

The posture change detection module 32 processes the strain sensor signal to identify the posture of the user (including lying on the bed 4 in a supine, prone or side position, sitting on the bed 4, or not being on the bed 4 at all). When the posture change detection module 32 determines that the posture of the user has changed from a lying posture to a sitting posture, the posture change detection module 32 outputs a corresponding signal to the baroreceptor reflex indication determination module 34.

When the user gets off the bed 4 and stands up, it will no longer be possible to extract a heart rate component from the signal output by the mechanical sensor(s) 6 (since the user is no longer in contact with the sensor(s) 6), and the signal from the mechanical sensor(s) 6 will indicate that the bed 4 is not occupied. Those skilled in the art will be aware of suitable algorithms that can be used to process signals received from mechanical sensor(s) on a bed 4 to determine the posture of a user lying on the bed 4. In particular, in the preferred embodiment where there is an array of mechanical sensors 6 on the bed 4, the act of a user sitting up in the bed 4 from a lying position will result in a significant change in the distribution of the forces acting on the array of mechanical sensors 6.

In addition, through extended usage of the apparatus 2, it is possible for the apparatus 2 to be self-learning, which means that the processor 12 can analyze the changes in the signals from the mechanical sensor(s) 6 that occur prior to an actual exit from the bed 4 and to use this analysis to adapt the algorithm used in the posture change detection module 32 (and posture change detection module 38 described below) to determine whether a bed exit is likely to take place. Such a self-learning system is described in WO 2010/029466, entitled "Bed Exit Warning System", the content of which is hereby incorporated by reference.

In a preferred embodiment, the posture change detection module 32 also outputs the posture change signal to the camera 8. This signal causes the camera 8 to be activated so that it can monitor the user from the sitting position to the standing position. As the camera 8 will be deactivated while the user is lying on the bed 4 (for example sleeping), the power consumption of the apparatus 2 can be reduced.

The signal (i.e. a series of images) output by the camera 8 is provided to a heart rate detection module 36 and a posture change detection module 38. The heart rate detection module 36 processes the images to determine the heart rate of the user while they are sitting on the edge of the bed 4 or standing upright next to the bed 4, and outputs a signal indicating the detected heart rate to the baroreceptor reflex indication determination module 34. As indicated above, the camera 8 and this module 36 can act as a remote PPG.

The posture change detection module 38 processes the series of images output by the camera 8 to determine the posture of the user (i.e. sitting on the edge of the bed 4 or standing next to the bed 4), and outputs a signal to the baroreceptor reflex indication determination module 34 when it is determined that the user has moved from a sitting position on the edge of the bed 4 to a standing position. Techniques and algorithms for recognizing the posture of the human body using camera images are well known. In a preferred embodiment, the algorithm used to process the camera images also needs to achieve face recognition, and distinguish between sitting and standing postures.

One paper describing an exemplary method for face detection is "Face Recognition with Support Vector Machines: Global versus Component-based Approach", B. Heisele et al., Computer Vision, 2001, the content of which is hereby incorporated by reference. In brief, face detection involves using features of the image (e.g., pixel values or gradient values) as input to a classifier, such as a Support Vector Machine, which is then trained on a training database containing face and non-face images. The classification can be applied to whole faces, or to individual components of faces.

One paper describing an exemplary method for distinguishing between sitting and standing postures is "Sit to Stand Detection and Analysis", S. Allin and A. Mihailidis in AAAI Fall Symposium Series 2008 the content of which is hereby incorporated by reference. In brief, the detection of moving from a sitting to a standing posture involves the extraction of features from input images and relating them to one of the two body positions. Image features include features from foreground silhouettes, such as Hu invariant moments. The recognition of the pose from the image features is achieved through training a classifier, using a training data set of camera images of users sitting on the edge of the bed 4 and subsequently standing up. The classifier can be any machine learning method, such as a classification tree, neural network, or support vector machine.

The baroreceptor reflex indication determination module 34 uses the heart rate measurements made by module 30 that detects the heart rate from the mechanical (strain) sensor signals and module 36 that detects the heart rate from the camera images, along with the indications of the posture changes provided by modules 32 and 38 to determine the indication of the baroreceptor reflex of the user.

In one embodiment, the indication of the baroreceptor reflex of the user comprises a measure of the change in the heart rate of the user as they moved from the lying position to the sitting position, a measure of the change in the heart rate of the user as they moved from the sitting position to the upright position, and/or a measure of the total heart rate change from the lying position to the upright position. These measures can be the change in the resting heart rate at each of the postures (the resting heart rate being the relatively constant value for the heart rate of the user when they have been in a particular posture for a few minutes), but preferably these measures can be the maximum change in the heart rate that occurs during, or shortly after, the transition between each of the postures.

Alternative (indirect) measures of the baroreceptor reflex that can be determined include the time it takes to get out of bed 4, and respiration rate. A decreased functioning of the baroreceptor reflex may result in a longer time to get out of bed 4, as the user needs to pause after the lying-sitting change and sitting-standing change. The respiration rate could also be extracted from the signals provided by the mechanical sensor(s) 6 and/or the camera 8, as respiration results in oscillatory mechanical forces that are greater than those produced by the action of the heart. This would allow breathing rate to be correlated with baroreceptor reflex functioning. This could be useful since slower breathing is known to increase baroreceptor reflex sensitivity in heart failure patients.

Figure 4:
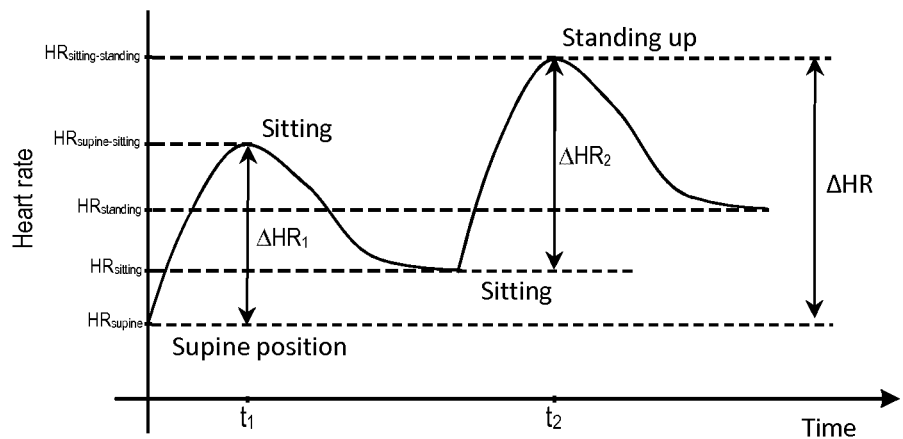
FIG. 4 is a graph illustrating the change in heart rate measured using the apparatus in FIGS. 1, 2 and 3.

FIG. 4 shows an illustrative graph of the heart rate output by the two heart rate detection modules 30, 36 as a user moves from a lying position to sitting on the edge of the bed 4 to standing up. In this example, the user sat on the edge of the bed 4 for approximately one minute, before taking about one minute to stand up and allow the heart rate to drop to a resting standing heart rate level. Thus, it can be seen that the heart rate increases from a resting heart rate level when the user is in a supine position (indicated by $HR_{supine}$) to a peak heart rate (indicated by $HR_{supine\text{-}sitting}$ at time $t_1$) as, or shortly after, the user moves from the supine position to a sitting position. The change in heart rate from the resting heart rate in the supine position ($HR_{supine}$) to the peak heart rate ($HR_{supine\text{-}sitting}$) is denoted $\Delta HR_1$ and provides an indication of the strength of the baroreceptor reflex in the user. Following the peak heart rate at time $t_1$, the heart rate decreases to a resting heart rate level for the sitting position (indicated by $HR_{sitting}$).

As, or shortly after, the user moves from the sitting position to a standing position, the heart rate then increases from the sitting resting heart rate ($HR_{sitting}$) to a peak heart rate (indicated by $HR_{sitting\text{-}standing}$ at time $t_2$). The change in heart rate from the resting heart rate in the sitting position ($HR_{sitting}$) to the peak heart rate ($HR_{sitting\text{-}standing}$) is denoted $\Delta HR_1$ and provides another indication of the strength of the baroreceptor reflex in the user. Following the peak heart rate at time $t_2$, the heart rate decreases to a resting heart rate level for the standing position (indicated by $HR_{standing}$).

Yet another indication of the baroreceptor reflex in the user can be provided by the change in the heart rate from the supine rest heart rate level ($HR_{supine}$) to the peak in the heart rate that occurs when the user is standing up from a sitting position ($HR_{sitting\text{-}standing}$). This heart rate change is denoted $\Delta HR$ in FIG. 4.

Typically, the heart rate increases to a peak value within 5 to 10 seconds after sitting or standing up. It then takes approximately one minute for the heart rate to drop to a resting level. The table below gives some indications of heart rates immediately after and at resting level for the 3 positions for healthy persons. These data have been obtained from Jones et al., 2003, "Changes in heart rate and R-wave amplitude with posture", Chinese Journal of Physiology.

| Postural change | Before | Peak | Resting level |
| --- | --- | --- | --- |
| Lying to sitting | 67 | 85 | 72 |
| Sitting to Standing | 72 | 89 | 79 |

In an alternative embodiment to that described above, the camera 8 can be active all the time the apparatus 2 is active and the heart rate detection module 36 can operate to detect the heart rate, even when the user is lying on the bed 4. The posture change detection module 38 can also operate to determine if the user is lying on the bed. In this embodiment, as the apparatus 2 will need to work in conditions of low light (e.g. in the morning before the user wakes/gets up), a sufficient amount of light must be provided for the PPG processing to work, In which case, a non-obtrusive light source, e.g., infra-red, could be used. The heart rate measurements from the camera images can be used in combination with the heart rate measurements determined from the strain sensor 6 to provide a single measure of the heart rate of the user. Alternatively, the measurements obtained from the strain sensor signal can be used to calibrate the measurements obtained using the camera images so that subsequent measurements by the camera 8 when the user is no longer in contact with the bed 4 (i.e. they are standing) are reasonably accurate.

It will be appreciated that in the preferred embodiment where the camera 8 is only activated once it has been determined that the user has sat up on the bed 4, the measurements of the heart rate determined from the strain sensor signal while the user is sitting on the bed 4 can be used to calibrate the measurements of the heart rate determined from the camera images before the user stands up.

In this calibration, the heart rate during sitting on the edge of the bed 4 as measured with the camera 8 could, for example, be multiplied with a factor such that it matches the heart rate as measured with the mechanical (strain) sensor 6 in the same body position. This calibration factor should then also be applied to the heart rate obtained with the camera 8 while the user is standing. After this calibration, the total heart rate change (subtracting the heart rate during lying on the bed 4 as measured by the mechanical (strain) sensor 6 from the heart rate measured by the camera 8 during standing) can provide a more accurate result.

It will be appreciated that in the embodiment where the camera 8 is active all the time, the calibration technique above can be extended to include the heart rates extracted while the user is lying on the bed 4.

In alternative embodiments of the invention, the apparatus 2 can comprise a single sensor for monitoring the posture of the user on the bed 4 and for determining the heart rate of the user. In one of these embodiments, the camera 8 can be omitted from the apparatus 2 described above, in which case the apparatus 2 determines the indication of the baroreceptor reflex of the user using just the measurements of the heart rate of the user in the lying and sitting positions from the mechanical sensor(s) 6. This embodiment could be used for users that are unable to stand up as a result of a medical condition. In an alternative one of these embodiments, the single sensor 6 is a camera, and the images obtained by the camera are used to determine the posture of the user (i.e. lying on the bed 4, sitting on the bed 4 or standing by the bed 4) and the heart rate of the user in each of those postures.

Figure 5:
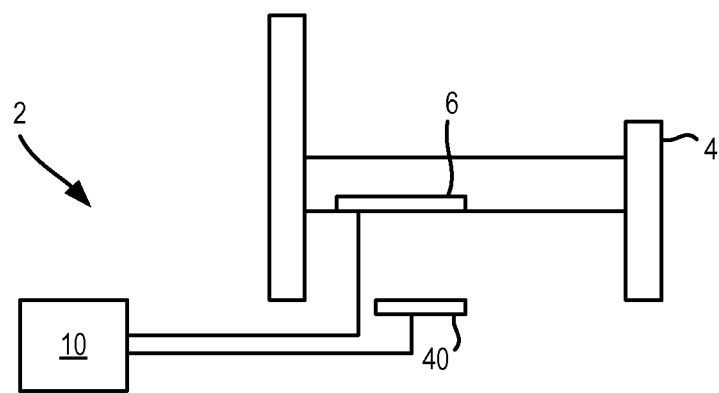
FIG. 5 shows a bed and an apparatus according to another embodiment of the invention.

In another embodiment of the invention, which is illustrated in FIG. 5, the camera 8 can be omitted from the apparatus 2, and measurements of the heart rate of the user in the standing position can be obtained using a second mechanical sensor 40 that is placed on the floor near to the bed 4 and that measures the movements/reaction force of the user during and after standing up. As with the mechanical sensor 6 that is integrated into the bed 4, the second mechanical sensor 40 can comprise one or more strain sensors, strain gauges, pressure sensors, piezoelectric sensors, resistive force sensors, load cells, and electret foil sensors, that measure the movements/reaction force of the user. The measurements from the second mechanical sensor 40 can be processed to determine the heart rate of the user in a similar way to the measurements from the first mechanical sensor 6. Explicit posture detection processing could be omitted as the assumption is made that if a non-zero signal is being output by the second mechanical sensor 40 then the user must be standing on the mechanical sensor 40.

In a yet further embodiment of the invention, instead of a camera 8, the second sensor can make use of Doppler radar techniques to remotely monitor the heart rate of the user while they are lying on the bed 4, sitting on the bed 4 and/or standing by the bed 4. Doppler radar techniques work on the basis that a radio frequency wave reflected from a moving surface undergoes a frequency shift proportional to the surface velocity (this is the Doppler effect). If the surface is periodically moving, such as the chest wall of a user as a result of cardiac and respiratory activity, the transmitted and reflected waves can be used to derive a low-frequency component that is proportional to the chest movement. Heart and respiratory rates can be derived from peaks in the frequency spectrum of this signal. As with the camera 8 described above, the Doppler radar sensor can be active all the time, or it can be activated when the first sensor 6 detects that the user has moved from a lying position to a sitting position on the bed 4.

In yet another embodiment of the invention, rather than a mechanical sensor, the first sensor 6 can be an optical sensor 6 that comprises one or more light emitting components (such as LEDs) and light detectors (such as photodetectors) that are placed underneath the mattress of the bed 4. This sensor optically senses movement-induced changes in the mattress of the bed 4. These sensors work by emitting light into the mattress and measuring the intensity of the light that is scattered back through the mattress over time. Any type of movement (i.e. respiratory movement, cardiac vibrations, as well as any other body movements) of the person lying on the mattress causes slight deformations of the mattress. Through this change in geometry, the optical properties of the mattress change which in turn causes a change in the intensity of light which is reflected or scattered back to the light detector. By recording the light intensity over time, a curve containing respiratory, cardiac and other activity can be obtained. Furthermore, in some embodiments the second sensor 8 can be an optical sensor that is placed beneath a mat on the floor by the bed 4 to detect the heart rate of the user when the user is standing by the bed 4.

One particular application for the apparatus 2 is remote monitoring of heart failure patients. Patients with heart failure are more likely to fall due to orthostatic hypotension and/or reduced baroreceptor reflex. The apparatus 2 can advantageously be used to remotely monitor changes in the baroreceptor reflex of the patient over time. These changes can be reviewed by a medical professional, and any deterioration in this reflex identified.

The apparatus 2 can also be used to provide an indication of whether a person is at an increased risk of falling. If it is determined that the person has an abnormal baroreceptor reflex, or it is determined that there has been a detrimental change in the baroreceptor reflex over time, the apparatus 2 can provide an indication that the person is at an increased risk of falling.

Therefore, there is provided an apparatus and method for monitoring the baroreceptor reflex of a user that can provide an indication of the baroreceptor reflex of the user using non-invasive and contactless measurements during a change in posture of the user from a lying position to a sitting position, and preferably also from the sitting position to a standing position.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for use in monitoring the baroreceptor reflex in a user, the apparatus comprising:
  one or more sensors configured to generate output signals conveying information related to a position of the user and information related to a heart rate of the user;
  a processor configured to:
    determine, based on output signals, when the user moves from a lying position on a bed to a sitting position;
    determine a heart rate when the user is lying, determine a heart rate when the user is sitting, and calculate a change between the heart rates of the user that occurs as a result of moving from the lying position to the sitting position; and
    provide an indication of the baroreceptor reflex of the user based on the calculated change in the heart rate of the user; and
  a display configured to display the indication of the baroreceptor reflex of the user.

2. The apparatus of claim 1, wherein the processor is configured to calculate the change in the heart rate of the user that occurs as a result of moving from the lying position to the sitting position as the change in the heart rate determined while the user is in the lying position on the bed to a maximum heart rate that occurs as a result of moving from the lying position to the sitting position.

3. The apparatus of claim 1, wherein the one or more sensors is configured to be attached to the bed and wherein the output signals represent movement of the user on the bed.

4. The apparatus of claim 1, wherein the one or more sensors comprise one or more of: a strain sensor, a strain gauge, a pressure sensor, a piezoelectric sensor, a resistive force sensor, a load cell, an electret foil sensor, a sensor for optically sensing movement-induced changes in a part of the bed, a camera, and/or a Doppler radar sensor.

5. The apparatus of claim 1, further comprising:
  an array of sensors adapted to be placed at different locations in the bed, configured to generate output signals conveying information related to the position of the user, and wherein
  the processor is further configured to determine when the user moves from the lying position on the bed to the sitting position based on the output signals from the array of sensors.

6. The apparatus of claim 1, further comprising:
  one or more additional sensors configured to generate additional output signals conveying information related to the position of the user, the one or more additional sensors being located proximate to the bed, and wherein
  the processor is further configured to:
    determine when the user moves to a standing position;
    determine the change in the heart rate of the user that occurs as a result of moving from the sitting position to the standing position; and
    provide an indication of the baroreceptor reflex of the user based on the change in the heart rate of the user.

7. The apparatus of claim 6, wherein the processor is configured to determine the change in the heart rate of the user that occurs as a result of moving from the sitting position to the standing position as the change in the heart rate determined while the user is in the sitting position to a maximum heart rate that occurs as a result of moving from the sitting position to the standing position.

8. The apparatus of claim 6, wherein the processor is further configured to determine the change in the heart rate determined while the user is in the lying position on bed to a maximum heart rate that occurs as a result of moving from the lying position to the standing position.

9. The apparatus of claim 6, wherein the processor is configured to activate the one or more additional sensors responsive to determining that the user has moved from the lying position on the bed to the sitting position.

10. The apparatus of claim 6, wherein the one or more additional sensors is configured to be located near the bed and the one or more additional sensors is configured to measure the movements of the user while the user is in a standing position.

11. The apparatus of claim 10, wherein the one or more additional sensors comprise one or more of a camera, a Doppler radar sensor, a sensor for optically sensing movement-induced changes in a mat near the bed, a strain sensor, a strain gauge, a pressure sensor, a piezoelectric sensor, a resistive force sensor, a load cell, and/or an electret foil sensor.

12. The apparatus of claim 6, wherein the processor is configured to calibrate the additional output signals by the one or more additional sensors when the user is in a sitting position on the bed using the heart rate determined from the output signals by the one or more sensors when the user is in the sitting position.

13. The apparatus of claim 1, wherein the processor is further configured to determine a respiration rate of the user based on the output signals by the one or more sensors.

14. A method of monitoring the baroreceptor reflex in a user, the method comprising:
  receiving, from one or more sensors, output signals conveying information related to a position of the user and information related to a heart rate of the user;
  determining, with a processor, based on the output signals when the user moves from a lying position on a bed to a sitting position;
  determining a heart rate when the user is lying, determining a heart rate when the user is sitting, and calculating a change between the heart rates of the user that occurs as a result of moving from the lying position to the sitting position;
  providing an indication of the baroreceptor reflex of the user based on the calculated change in the heart rate of the user; and
  displaying, with a display, the indication of the baroreceptor reflex of the user.

15. The method of claim 14, wherein the display is further configured to display an alert indicating that the heart rate of the user is abnormal.

* * * * *